US009211078B2

(12) United States Patent
Meggiolaro et al.

(10) Patent No.: US 9,211,078 B2
(45) Date of Patent: Dec. 15, 2015

(54) PROCESS AND DEVICE FOR BRAIN COMPUTER INTERFACE

(75) Inventors: Marco Antonio Meggiolaro, Rio de Janeiro (BR); Alexandre Ormiga Galvao Barbosa, Rio de janeiro (BR)

(73) Assignee: Faculdades Católicas, a nonprofit association, maintainer of the Pontificia Universidade Católica of Rio de Janeiro, Rio de Janeiro (BR)

(*) Notice: Subject to any disclaimer, the term of this patent is extended or adjusted under 35 U.S.C. 154(b) by 791 days.

(21) Appl. No.: 12/875,544

(22) Filed: Sep. 3, 2010

(65) Prior Publication Data

US 2012/0059273 A1    Mar. 8, 2012

(51) Int. Cl.
*A61B 5/04*    (2006.01)
*A61B 5/048*    (2006.01)
*A61B 5/00*    (2006.01)
*G06F 3/01*    (2006.01)

(52) U.S. Cl.
CPC ............. *A61B 5/048* (2013.01); *A61B 5/7203* (2013.01); *A61B 5/7264* (2013.01); *G06F 3/015* (2013.01)

(58) Field of Classification Search
CPC .... A61B 5/048; A61B 5/7264; A61B 5/7203; G06F 3/015
USPC .................................................. 600/544–545
See application file for complete search history.

(56) References Cited

U.S. PATENT DOCUMENTS

| 2003/0093129 | A1* | 5/2003 | Nicolelis et al. | 607/45 |
| 2004/0267320 | A1* | 12/2004 | Taylor et al. | 607/2 |
| 2010/0137734 | A1* | 6/2010 | Digiovanna et al. | 600/545 |
| 2012/0101402 | A1* | 4/2012 | Nguyen | 600/544 |

OTHER PUBLICATIONS

Millan, et al. "A Local Neural Classifier for the Recognition of EEG Patterns Associated to Mental Tasks," 2002, IEEE Trans. on Neural Networks, vol. 13, No. 3, pp. 678-686.*

* cited by examiner

*Primary Examiner* — Navin Natnithithadha
*Assistant Examiner* — Eric Messersmith
(74) *Attorney, Agent, or Firm* — Laurence P. Colton; Smith Risley Tempel Santos LLC (57) ABSTRACT

A brain computer interface as an alternative communication channel to be used in various applications, such as robotics. In one embodiment of the invention, there is provided a process for the analysis and conversion of EEG signals obtained from the brain into movement commands through electric and/or mechanical devices. The process of the present invention provides substantial advantages over the similar systems/techniques known in the art, such as a 91% average hit rate, obtained in attempts to control a mobile robot. In other embodiment of the invention, there is provided an apparatus comprising: means for obtaining brain signals; an electroencephalograph (EEG); and means for transducing said signals into functional commands useful in several applications. Said means for transducing mental signals is the core of the invention and provides a number of technical advantages over the similar systems/techniques known in the art of identifying mental activities.

11 Claims, 5 Drawing Sheets

PROCESS AND DEVICE FOR BRAIN COMPUTER INTERFACE

BACKGROUND OF THE INVENTION

1. Field of the Invention

The present invention is in the field of brain-controlled devices and processes. More specifically, the present invention provides a brain computer interface as an alternative communication channel to be used in various applications, such as robotics. In one embodiment of the invention, there is provided a process for the analysis and conversion of EEG signals obtained from the brain into movement commands through electric and/or mechanical devices. The process of the present invention provides substantial advantages over the similar systems/techniques known in the art, such as a 91% average hit rate, obtained in attempts to control a mobile robot. In other embodiment of the invention, there is provided an apparatus comprising: means for obtaining brain signals; an electroencephalograph (EEG); and means for transducing said signals into functional commands useful in several applications. Said means for transducing mental signals is the core of the invention and provides a number of technical advantages over the similar systems/techniques known in the art of identifying mental activities.

2. Prior Art

The development of interfaces between humans and machines has been an expanding field in the last decades. It includes several interfaces using voice, vision, haptics, electromyography, electroencephalography (EEG), and combinations among them as a communication support.[1] A system that analyzes brainwaves to derive information about the subjects' mental state is called a Brain Computer Interface (BCI).[2]

People who are partially or totally paralyzed (e.g., by amyotrophic lateral sclerosis (ALS) or brainstem stroke) or have other severe motor disabilities can find a BCI as an alternative communication channel.[3] BCI systems are used to operate a number of brain-actuated applications that augment people's communication capabilities, provide new forms of education and entertainment, and also enable the operation of physical devices.[2]

There are two types of BCI's: invasive, which are based on signals recorded from electrodes implanted over the brain cortex (requiring surgery), and non-invasive, based on the analysis of EEG phenomena associated with various aspects of brain function.[1]

Birbaumer measured slow cortical potentials (SCP) over the vertex (top of the scalp).[4] SCP are shifts in the depolarization level of the upper cortical dendrites, which indicate the overall preparatory excitation level of a cortical network. Other groups looked at local variations of the EEG rhythms. The most used of such rhythms are related to the imagination of movements, recorded from the central region of the scalp overlying the sensorimotor and pre-sensorimotor cortex. In this respect, there are two main paradigms. Pfurtscheller's team worked with event-related desynchronization (ERD) computed at fixed time intervals after the subject is commanded to imagine specific movements of the limbs.[5,6] Alternatively, Wolpaw and coworkers analyzed continuous changes in the amplitudes of the mu (8-12 Hz) or beta (13-28 Hz) rhythms.[7]

Finally, in addition to motor-related rhythms, Anderson and Millán analyzed continuous variations of EEG rhythms, but not only over the sensorimotor cortex and in specific frequency bands.[8,9] The reason is that a number of neurocognitive studies have found that different mental activities (such as imagination of movements, arithmetic operations, or language) activate local cortical areas at different extents. The insights gathered from these studies guide the placement of electrodes to get more relevant signals for the different tasks to be recognized.

BCI applications include control of the elements in a computer-rendered environment such as cursor positioning[1,3] or visiting of a virtual apartment.[10] spelling software,[11] and command of an external device such as a robot[12] or prosthesis.[13] Recent applications in Robotics are the control of a wheelchair[14-16] and the control of the Khepera mobile robot.[17]

The scientific literature which appears in the present invention is the following:

1. G. N. Garcia, "Direct brain-computer communication through scalp recorded EEG signals," Doctor's thesis, Department of Electricity, Ecole Polytechnique Fédérale de Lausanne, Switzerland, 2004.
2. J. d. R. Millán, Brain-Computer Interfaces, Handbook of Brain Theory and Neural Networks, 2nd ed., Cambridge, Mass., The MIT Press, 2002.
3. J. R. Wolpaw, D. J. McFarland, T. M. Vaughan, "Brain Computer Interface Research at the Wadsworth Center," IEEE Transactions on Neural Systems and Rehab. Eng., vol. 8, pp. 222-226, 2000.
4. N. Birbaumer, "A spelling device for the paralyzed," Nature, vol. 398, pp. 297-298, 1999.
5. J. Kalcher, "Graz brain-computer interface II," Med. & Biol. Eng. & Comput., vol. 34, pp. 382-388. 1996.
6. B. Obermaier, C. Neuper, C. Guger, G. Pfurtscheller, "Information Transfer Rate in a Five-Classes Brain Computer Interface," IEEE Transactions on Neural Systems and Rehabilitation Engineering, vol. 9, no. 3, pp. 283-288, 2001.
7. J. R. Wolpaw, D. J. McFarland, "Multichannel EEG-based brain-computer communication," Electroenceph. Clin. Neurophysiol., vol. 90, pp. 444-449, 1994.
8. C. W. Anderson, "Effects of variations in neural network topology and output averaging on the discrimination of mental tasks from spontaneous EEG," Journal of Intelligent Systems, vol. 7, pp. 165-190, 1997.
9. J. d. R. Millán, Brain-Computer Interfaces, Handbook of Brain Theory and Neural Networks, Second edition, Cambridge, Mass., The MIT Press, 2002.
10. J. D. Bayliss, "Use of the Evoked Potential P3 Component for Control in a Virtual Apartment," IEEE Transactions Rehabilitation Engineering, vol. 11, no. 2, pp. 113-116, 2003.
11. B. Obermaier, G. Müller, G. Pfurtscheller, "'Virtual Keyboard' controlled by spontaneous EEG activity," Proc. of the Int. Conference on Artificial Neural Networks, Heidelberg: Springer-Verlag, 2001.
12. J. d. R. Millán and J. Mourino, "Asynchronous BCI and local neural classifiers: an overview of the adaptive brain interface project," IEEE Transactions on Neural Systems and Rehabilitation Engineering, vol. 11, no. 2, pp. 159-161, 2003.
13. G. Pfurtscheller, C. Neuper, G. R. Muller, B. Obermaier, G. Krausz, A. Schlogl, R. Scherer, B. Graimann, C. Keinrath, D. Skliris, M. Wortz, G. Supp, C. Schrank, "Graz-bci: State of the Art and Clinical Applications," IEEE Transactions on Neural Systems and Rehabilitation Engineering, vol. 11, no. 2, pp. 177-180, 2003.
14. B. Rebsamen, E. Burdet, C. Guan, C. L. Teo, Q. Zeng, M. Ang, C. Laugier, "Controlling a wheelchair using a BCI with low information transfer rate," IEEE International Conference on Rehabilitation Robotics (ICORR), pp. 1003-1008, 2007.

15. F. Galán, M. Nuttin, E. Lew, P. W. Ferrez, G. Vanacker, J. Philips and J. d. R. Millán, "A Brain-Actuated Wheelchair: Asynchronous and Non-Invasive Brain-Computer Interfaces for Continuous Control of Robots," Clinical Neurophysiology, vol. 119, pp. 2159-2169, 2008.

16. I. Iturrate, J. Antelis, A. Kübler, J. Minguez, "A noninvasive brain-actuated wheelchair based on a P300 neurophysiological protocol and automated navigation," IEEE Transactions on Robotics, vol. 99, pp. 1-14, 2009.

17. J. d. R. Millán, F. Renkens, J. Mouriño, W. Gerstner, "Noninvasive Brain-Actuated Control of a Mobile Robot by Human EEG," IEEE Transactions on Biomedical Engineering, vol. 51, no. 6, pp 1026-1033, 2004.

18. A. R. Cotrina, "Sistemas de adquisición y procesamiento de las señales del cerebro," B.Sc. Thesis, Departamento de Ingeniería Eléctrica y Electrónica, Universidad Nacional de Ingeniería, Lima, Peru, 2003.

19. M. Benning, S. Boyd, A. Cochrane, D. Uddenberg, "The Experimental Portable EEG/EMG Amplifier," ELEC 499A Report, University of Victoria, Faculty of Engineering, August 2003.

20. National Instruments, "Build Your Own NI Compact-DAQ System." [Online]. Available: http://ohm.ni.com/advisors/compactdaq 21. C. Tandonnet, B. Burle, T. Hasbroucq, F. Vidal, "Spatial enhancement of EEG traces by surface Laplacian estimation: comparison between local and global methods," Clinical Neurophysiology, vol. 116, no. 1, pp. 18-24, 2005.

22. P. Jahankhani, V. Kodogiannis, K. Revett, "EEG signal classification using wavelet feature extraction and neural networks," IEEE John Vincent Atanasoff International Symposium on Modern Computing, pp. 120-124, 2006.

23. M. Van de Velde, G. Van Erp, P. J. M. Cluitmans, "Detection of muscle artifact in the normal human awake EEG," Electroencephalography and Clinical Neurophysiology, vol. 107, no. 2, pp. 149-158, 1998.

24. D. R. Achanccaray, M. A. Meggiolaro, "Brain Computer Interface Based on Electroencephalographic Signal Processing," XVI IEEE International Congress of Electrical, Electronic and Systems Engineering—INTERCON 2009, Arequipa, Peru, 2009.

25. A. O. G. Barbosa, D. R. Achanccaray, M. Vellasco, M. A. Meggiolaro, R. Tanscheit, "Mental Tasks Classification for a Noninvasive BCI Application", 19th International Conference on Artificial Neural Networks, ICANN'09, Limassol, Cyprus, 2009.

26. F. Findji, P. Catani, C. Liard, "Topographical distribution of delta rhythms during sleep: Evolution with age," Electroencephalography and Clinical Neurophysiology, vol. 51, no. 6, pp. 659-665, 1981.

27. Endurance R/C, "PCTx—PC to Transmitter Interface." [Online]. Available: http://www.endurance-rc.com/pctx.html.

To the best knowledge of the inventors, neither any document anticipating the present invention was found nor the combination of the existing ones even suggest the subject-matter of the invention.

BRIEF SUMMARY OF THE INVENTION

Briefly, the present invention comprises a process and a device for non-invasive BCI based on EEG analysis. In one preferred embodiment said device is used to control a mobile robot, wherein the control is provided through four different mental activities, such as imaginary movements of a specific limb. These activities are correlated with four robot movements, respectively. The interface classifies the user's mental activity, sending the corresponding command to activate the mobile robot. Note that the user does not need to be able to perform any movement; just imagining them is enough to activate the robot.

It is one of the objects of the present invention to provide an improved brain computer interface.

In one embodiment of the invention, being therefore, another of its objects, there is provided a process for brain controlled functions comprising the steps of: non-invasively obtaining brain signals through a set of electrodes; processing and recording said signals with an electroencephalograph (EEG); and transducing said signals into functional commands useful in several applications. The step of transducing signals (the interface) comprises EEG signal analyses, which extract features that can be classified as specific mental activities. The step of transducing signals preferably comprises three steps: signal preprocessing; different models of neural networks to classify mental activities; and usage of different classifiers implementations based on multiple trials classification. In a preferred embodiment of the process of the invention, the step of transducing signals comprises the following: first, a signal preprocessing is performed from the EEG data, filtering noise, using a spatial filter to increase the scalp signal resolution, and extracting relevant features; then, different classifier models based on neural networks are proposed, evaluated and compared; and then, two implementations of the developed classifiers, based on multiple trial classification, are proposed to improve the rate of successful commands through the interface.

In a preferred embodiment of the invention, there is provided a process for brain controlled functions comprising the steps of:
a) non-invasively obtaining brain signals;
b) processing said signals with an electroencephalograph (EEG); and
c) transducing said signals into functional commands by means of feature extraction from EEG signals, wherein said signals are classified as specific mental activities by:
  i) signal preprocessing;
  ii) implementation of classifying models; and
  iii) multiple trial classification to improve the rate of successful commands.

Figure 4:
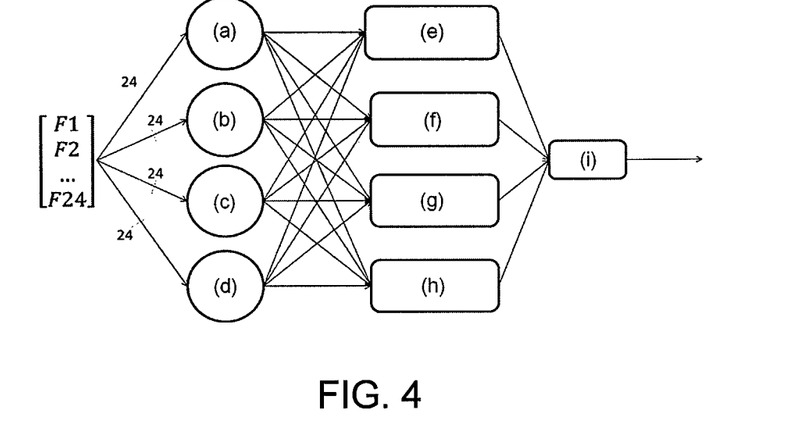
FIG. 4 shows the ensemble model, where (a) means "NET 1", (b) means "NET 2", (c) means "NET 3", (d) means "NET 4", (e) means "MEAN PATTERN 'RM'", (f) means "MEAN PATTERN 'LM'", (g) means "MEAN PATTERN 'UM'", (h) means "MEAN PATTERN 'DM'", (i) means "MAX".

In a preferred embodiment of the process of the invention, the step of classifying models comprises the consideration and evaluation of at least one or a combination of the following:

an ensemble of MLP artificial neural networks, which is proposed as a classifier due to its well-known performance for generalization. Such ensemble has the same number of MLP neural networks and patterns (for example, 4), and each one classifies better one of the patterns, resulting in a better classification when the responses of each neural network are combined. Such method can be, for example, the Ensemble of MLP Neural Networks with Driven Pattern Replication (MLP-DPR) (FIG. 4);

a system where a certain number of neural networks are used, one for each pattern. Each network classifies feature vectors as belonging or not to its respective pattern and associates a grade to measure the relation between these outputs. Such system can be, for example, the Modular Multi-Net System (MMN) (FIG. 5); when more than one neural network classifies a feature vector as belonging to its respective pattern, the classification is obtained as the one with higher output value.

an hierarchical structure where the first level classifies among merged patterns resulting from the union of confused patterns, and the second level classifies between the confused patterns when its respective merged pattern was pre-classified in the first level.

In a preferred embodiment of the process of the invention, the step of multiple trial classification to improve the rate of successful commands comprises two implementations of the proposed methods:

an implementation that uses the third system described before, such as Threshold implementation with MMN. Grades attributed to each output—corresponding to each pattern—are added to their respective grades in the next trial. When the grade sum of some pattern reaches a predetermined limit, that pattern is chosen and converted. If more than other pattern reaches the threshold at the same trial or if no pattern reaches the defined threshold within the maximum number of trials, then the command is classified as 'unclear' and no action is taken. The threshold value is defined according to the user's ability to generate patterns repeatedly;

an implementation which uses the third system described before, such as Statistical implementation with HM. Each trial is classified using the third model described before, for example the HM. For m different patterns, the occurrence of each one and the limit rate of occurrence are evaluated according to m. If the limit rate of occurrence of a pattern is reached, then it is chosen and converted. If the number of trials reaches a pre-specified number without choosing a pattern, then the command is classified as 'unclear' and no action is taken.

In another preferred embodiment of the process of the invention, the hit rate is of about 91% or higher, and/or the rate of wrong commands about 1.25% or lower, after 400 attempts to generate a control signal.

In another embodiment of the invention, being therefore, another of its objects, there is provided a device/apparatus for brain controlled functions comprising: means for non-invasively obtaining brain signals; an electroencephalograph (EEG); and means for transducing said signals into functional commands useful in several applications. In a preferred embodiment, said device is applied to the control of the movements of a 120 lb mobile robot by the brain, associating four different mental activities to robot commands.

In a preferred embodiment, the device of the invention provides the brain control of electromechanical devices/equipments, such as electric wheelchairs or robotic manipulators/prostheses.

In a another preferred embodiment, the device of the invention provides the brain control of a software that allows the user to scroll through a function menu with many functions using the mental activities, and selecting the desired one by a mental activity or by an eye blink. The software can use all brain activities or only a subset of only two or three activities, to decrease the time response while increasing the system hit rate very close to 100%.

These and other objects, features and advantages of the invention will be more readily understood by the detailed description of the invention when taken in connection with the appended figures.

DETAILED DESCRIPTION OF PREFERRED EMBODIMENTS

The present invention provides an improved brain computer interface. An inventive concept of the invention is the means for transducing signals obtained from the brain, said transducing means comprising improved algorithms.

The invention provides a process for brain controlled functions comprising the steps of: non-invasively obtaining brain signals; processing said signals with an electroencephalograph (EEG); and transducing said signals into functional commands useful in several applications. The step of transducing signals (the interface) comprises EEG signal analyses, which extract features that can be classified as specific mental activities. The step of transducing signals preferably comprises three steps: signal preprocessing; different models of neural networks to classify mental activities; and usage of different classifiers implementations based on multiple trials classification. In a preferred embodiment of the process of the invention, the step of transducing signals comprises the following: first, a signal preprocessing is performed from the EEG data, filtering noise, using a spatial filter to increase the scalp signal resolution, and extracting relevant features; then, different classifier models are proposed, evaluated and compared; and then, two implementations of the developed classifiers are proposed to improve the rate of successful commands to the mobile robot. In one of the implementations, a 91% average hit rate is obtained, with only 1.25% wrong commands after 400 attempts to control the mobile robot.

The invention also provides a device/apparatus for brain controlled functions comprising: means for obtaining brain signals; an electroencephalograph (EEG); and means for transducing said signals into functional commands useful in several applications. In a preferred embodiment, said device is applied to the control of the movements of a 120 lb mobile robot by the brain, associating four different mental activities to robot commands.

The details and preferred embodiments set forth below are intended to facilitate the reproduction of the invention, and should therefore be understood as being merely illustrative, without restricting the scope of the invention. Accordingly, the preferred embodiments of the invention are referred to as the movement of a mobile robot through the analysis, interpretation and conversion of brain waves to this movement, although there are many other applications of the invention.

EXAMPLE 1

Preprocessing

Preprocessing is performed in a PC notebook or in a dedicated electronic processing board in basically four steps: noise filtering, spatial filtering, feature extraction and subject-artifact detection.

A. Electrical Noise

Most sources of external noise can be avoided by appropriately controlling the environment in which the measurement takes place. But not all interferences can be eliminated in this way. Even if the electronic components are enclosed in a metal box and properly grounded, EEG signals are not totally free from power line and other noises. Thus, a low pass Butterworth eighth order digital filter with cut-off frequency of 35 Hz was designed to eliminate any residual noise, keeping only the EEG frequencies of interest.

B. Spatial Filtering

Conventional monopolar electroencephalographic (EEG) recordings have a poor spatial resolution. The scalp potential distribution can be viewed as a 'blurred' copy of the original cortical potential distribution. However, a local estimation can be obtained, by Hjorth's method, computing the difference between the potential at each electrode site and the average potential of its nearest neighbors[21]

$$4 \cdot \frac{Vn - (VA + VB + VC)/3}{d^2} \quad (1)$$

where Vn is the potential recorded at the nodal electrode, VA, VB, VC are the potentials recorded at the surrounding electrodes, and d is the distance between the nodal and the surrounding electrodes.

C. Feature Extraction

Figure 1:
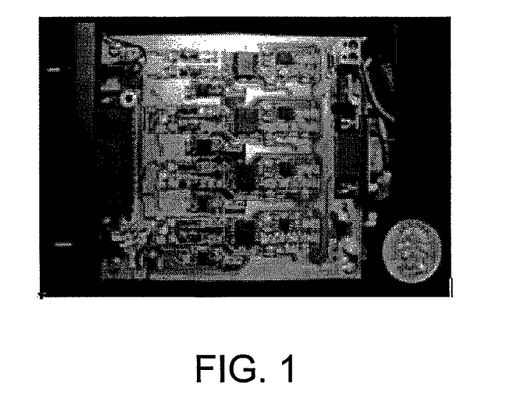
FIG. 1 is a photograph of a preferred embodiment of the device of the invention, showing details of miniaturized embedded version of the developed 8-channel electroencephalograph, used in the experiments.
Figure 2:
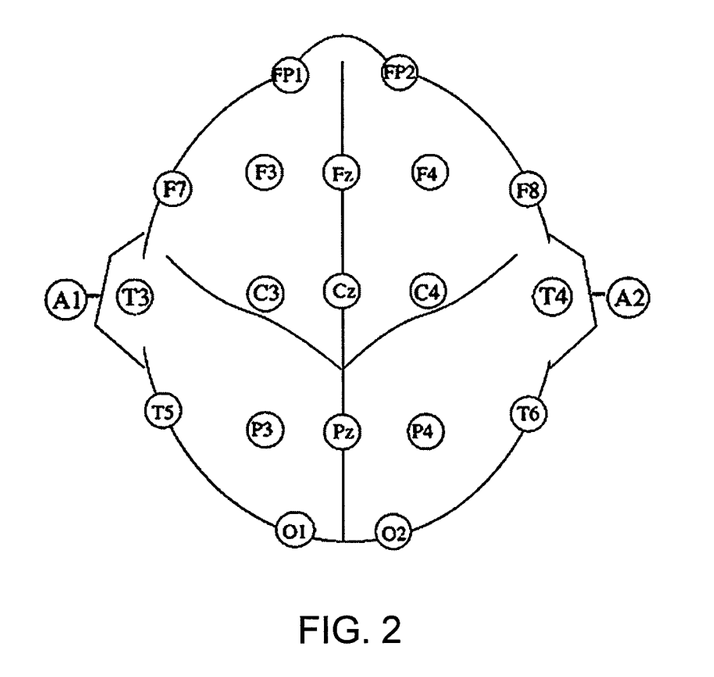
FIG. 2 presents the electrode positions from the International System 10-20.

Due to brain specialization, electrodes placed on the frontal (located near the pre-motor cortex area), center (at the motor cortex area) and parietal locations are chosen to acquire EEG signals. They correspond to F3, Fz, F4, C3, Cz, C4, P3 and P4 locations, according to the International System 10-20 of Electrode Placement, shown in FIG. 2.

Figure 3:
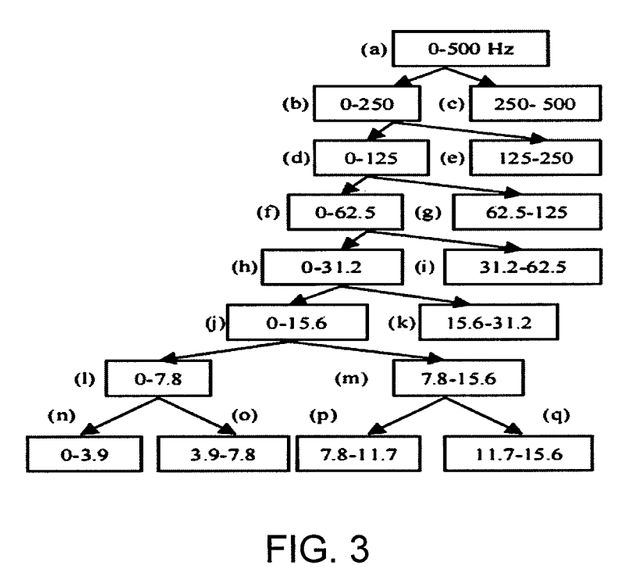
FIG. 3 shows the DWT decomposition of the frequency range, where letters from (a) to (q) means the frequency ranges of the brainwaves.

EEG signals from each one of the 8 channels are decomposed through a Discrete Wavelet Transform (DWT) until achieving the frequency range of the brainwaves. The DWT is applied in seven levels, shown in FIG. 3, to approximately represent the four principal frequency ranges of the brainwaves[22]:

Delta Band [0-4 Hz]: (n).
Theta Band [4-8 Hz]: (o).
Alpha Band [8-13 Hz]: (m).
Beta Band [13-30 Hz]: (k).

The chosen sample rate is 1 kHz, so the decomposition of frequency ranges begins in the range between 0 and 500 Hz.

Most mental tasks related to imagery movements show higher activity in the alpha and beta bands,[3] therefore these frequencies are chosen to be processed.

A Multi Layer Perceptron Neural Network is designed to evaluate the relevance of some extracted features from the selected levels from the DWT decomposition. In one embodiment of the present invention, a series of 10 datasets composed each by 700 EEG samples from the same subject is used for training, validation and further tests. Each sample is acquired within a period of 1 second, including information from 8 electrodes (channels). The user is asked to carry out 175 trials of each of the four imaginary movements: left arm, right arm, tongue and feet, totaling 700 samples. From this dataset, 400 trials are used for training, 100 for training validation, and 200 for testing.

A few features such as mean, zero-crossing and energy from different levels of the DWT are combined as feature vector inputs for the MLP neural network. The feature vector was chosen as the one that led to the highest number of correct classifications from the experiments.

The chosen feature vector VF is composed by the energies of the "m" (Alpha Band), "k" (Beta Band) and "h" (whole EEG spectrum) levels from the DWT decomposition. The energy E is defined as $$E = \frac{\sum_{i=1}^{n} V_{DWT,i}^2}{n} \quad (2)$$

where n is the length of the VDWT vector from the DWT decomposition from each chosen band from each of the 8 channels, and VDWT,i is the ith element of this vector.

Since there are 3 bands per each of the 8 channels, the chosen feature vector VF has 24 elements, corresponding to a mental task trial acquired during a period of 1 second.

D. Artifact Detection

The presence of eye movements, eye blinks and muscular artifacts in EEG signals can be easily detected from simple observation. As a matter of fact, each type of artifact has characteristics in time and frequency that make it distinguishable from regular EEG signals.[1]

The spectral content of ocular artifacts is mainly concentrated in the Theta Band (4-8 Hz), with relatively high amplitudes. They are more prominent at frontal pole electrodes, i.e., Fp1 and Fp2[23]. Artifacts can be considered as singular events in the time-frequency plane that appear randomly in EEG signals. Thus, due to their characteristics, they can be statistically detected in a dataset.

In this embodiment of the invention, only ocular artifacts are detected and removed from the training dataset. Detection is made computing the mean of the energy signal from the front electrodes (F3, F4 and Fz) at the "h" level from the DWT. Experiments showed that artifacts can be detected as the ones which are larger than 3 times the dataset deviation. Also, a third order Butterworth digital high-pass filter, with a 4 Hz cut-off frequency, is designed to attenuate ocular artifacts during the application.

EXAMPLE 2

Processing

Once EEG signals have been preprocessed in the computer to generate feature vectors, they are classified (in the same computer) as one of the four chosen mental tasks: imaginary movement of the right arm (Right Movement, RM), left arm (Left Movement, LM), tongue (Up Movement, UM, which will be associated to the robot moving forward) and feet (Down Movement, DM, associated to stopping the robot). These mental tasks were chosen due to their accentuated characteristics in brain activity, making them easy to correlate to a desired mobile robot action. In this embodiment of the invention, classifiers based on artificial neural networks are used.

In a previous work from the authors, Achanccaray compared a Probabilistic Neural Network (PNN) and a Multilayer Perceptron Neural Network (MLP).[24] The proposed method ended up using a PNN based on the DWT decomposition in the Delta Band, but with modest results.

The methods proposed before by Barbosa showed a very good performance in preliminary tests.[25] However, the number of experiments was not statistically significant—a very limited number of tests had been performed to validate the proposed methodology.

In one embodiment of the invention, an extensive experimental program consisting of 10 sets of 700 mental activities each is performed to properly evaluate the hit rate statistics. Four classification methods are considered and evaluated: the PNN Delta Band method,[24] and three novel methods based on improvements of the models presented in Barbosa: one ensemble of MLP models, one modular multi-net system, and one hierarchical model, described next.[25]

A. Ensemble of MLP Neural Networks with Driven Pattern Replication (MLP-DPR)

An ensemble of MLP artificial neural networks (FIG. 4) was developed in the present invention as a classifier for this problem, due to its well-known performance for generalization.[25] This ensemble is composed by four different MLP neural networks, where each one classifies better one of the four patterns RM, LM, UM and DM. Driven pattern replication in training dataset is used to create different neural networks. Networks specialized in each pattern are trained with their respective training feature vectors replicated four times, in addition to the other pattern feature vectors. Therefore, the same feature vector is applied to each neural network. The final classification is obtained combining the outputs of each member by their mean value, selecting then the higher average output.

B. Modular Multi-net System (MMN)

Figure 5:
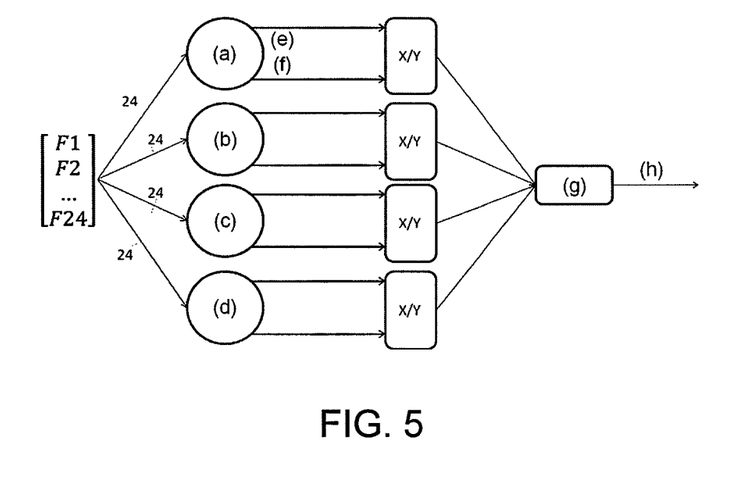
FIG. 5 illustrates the modular multi-net system, where (a) means "NET 'RM'", (b) means "NET 'LM'", (c) means "NET 'UM'", (d) means "NET 'DM'", (e) means "belongs", (f) means "does not belong", (g) means "MAX", and (h) means "answer".

In this system, four neural networks are used, see FIG. 5. Each network classifies feature vectors as belonging or not to its respective pattern. When more than one neural network classifies a feature vector as belonging to its respective pattern, the classification is obtained as the one with higher output value. In order to simplify the algorithm, a grade attributed to each pattern is calculated as the ratio between the two outputs of the neural networks ("belongs to group" output divided by the "does not belong to group" output).

C. Hierarchical Model (HM)

The hierarchical model has been proposed after evaluating the classification performance of the modular multi-net system (MMN). By analyzing the resulting confusion matrix of the MMN (Table I), it is verified that the majority of missed classification is between the UM and DM patterns.

TABLE I

Confusion matrix of the modular multi-net system

|    | DM | UM | RM | LM |
|----|----|----|----|----|
| DM | 27 | 13 | 4  | 6  |
| UM | 10 | 22 | 9  | 9  |
| RM | 2  | 2  | 40 | 6  |
| LM | 6  | 6  | 11 | 27 |

Figure 6:
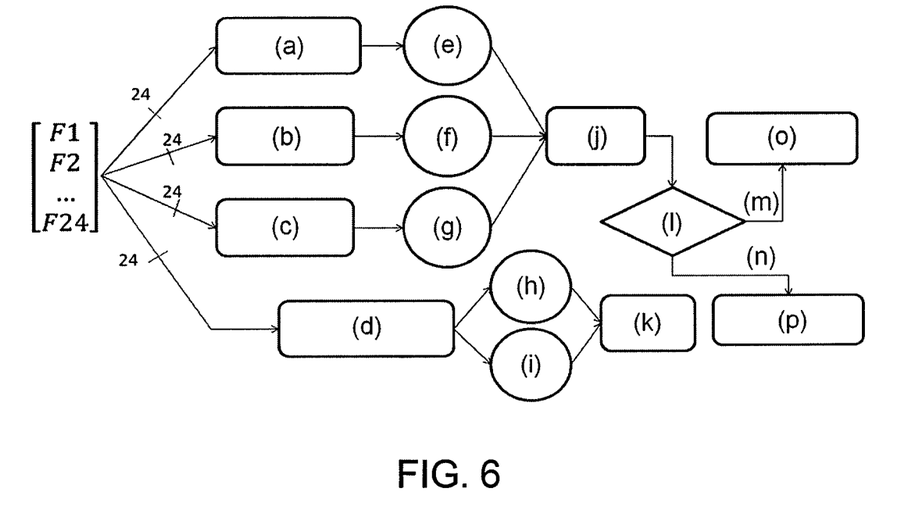
FIG. 6 presents the hierarchical model, where (a) means "NET RM", (b) means "NET LM", (c) means "NET 'UM or DM'", (d) means "NET 'UM'/'DM'", (e) means "RM", (f) means "LM", (g) means "'UM or DM'", (h) means "DM", (i) means "UM", (j) means "MAX 1st STEP", (k) means "MAX 2nd STEP", (l) means "UM or DM", (m) means "no", (n) means "yes", (o) means "PATTERN—MAX 1st STEP", (p) means "PATTERN—MAX 2nd STEP".

Therefore, a hierarchical structure is modeled, as shown in FIG. 6. It is composed of three classifiers in the first step, trained to recognize pattern as belonging or not belonging to RM, LM, and {UM or DM}. In the second step, another MLP neural network is used, to identify between UM and DM patterns when {UM or DM} has been pre-classified by its respective subsystem in the first step. The same feature vector is applied to all classifiers. The final system response depends on the first step classifiers. If the first step subsystem trained to identify {UM or DM} provides the highest output level among all subsystems, then the hierarchical system response is given by the second step MLP network classification (maximum value between the UM and DM outputs). Otherwise, the final response is provided by the first step subsystem with the highest output value. As a result, the new resulting confusion matrix (Table II) shows better results than the MMN model, increasing the classification hit rate. In the next section, the classifier models are experimentally evaluated and compared.

TABLE II

Confusion matrix of the hierarchical model

|    | DM | UM | RM | LM |
|----|----|----|----|----|
| DM | 28 | 12 | 4  | 6  |
| UM | 5  | 27 | 9  | 9  |
| RM | 2  | 2  | 40 | 6  |
| LM | 6  | 5  | 9  | 30 |

EXAMPLE 3

Classifier Experiments

The four classification methods described in the previous sections are evaluated with and without discarding ocular artifacts from the training dataset. The evaluation uses 2,000 mental activities, from the 200 test data from each of the 10 sets previously mentioned, obtained from a single user. Table III shows the hit rates of correct classifications for the 10 datasets with and without ocular artifact detection. It is seen that the preprocessing for ocular artifacts, present due to blinking or reading instructions on the test computer, does not lead to significant improvements in the hit rates.

TABLE III

Average hit rates of correct classifications

|         | Discarding Ocular Artifacts | Without Artifact Detection |
|---------|-----------------------------|----------------------------|
| PNN-DB  | 36%                         | 36%                        |
| MLP-DPR | 60%                         | 59%                        |
| MMN     | 61%                         | 59%                        |
| HM      | 65%                         | 63%                        |

As seen in Table III, the PNN-DB method results in a low average 36% hit rate. This low performance may be explained by the choice of the Delta Band, which is commonly related to deep sleep,[26] and possibly due to having discarded relevant electrodes such as C4 and Fz.

The other 3 methods present better hit rates, around 60%. However, such hit rates may still be insufficient for several brain-machine tasks. Therefore, it is not a good idea to use a single trial to be classified and converted into some robot action. Two different implementations of the proposed methods are considered to link the user and a robot, using multiple trials (and without the need to detect artifacts). Both implementations use consecutive trials of one second each, which are recorded, processed and combined to result in the final classification, as described next.

A. Threshold Implementation with MMN

In the threshold implementation, the modular multi-net (MMN) system is used, because it has a similar performance to MLP-DPR and HM, while providing a grade estimated in the same way to the four patterns (the HM, e.g., uses different networks, in addition to its division into two steps). Grades attributed to each output—corresponding to the four patterns RM, LM, UM and DM—are added to their respective grades in the next trial, until a threshold is reached by one pattern, when it is chosen and converted into a robot action. In this example, the highest grade at each trial is set as 3, and the threshold is defined as 5 (therefore, at least 2 trials are needed to reach the threshold), but other values can be chosen. If more than one pattern reaches the threshold at the same trial or if no pattern reaches the defined threshold within, e.g., 15 trials, then the command is classified as 'unclear' and no action is taken.

The threshold value is defined by user, correlated to his/her ability to concentrate on the imaginary movements. During the first time using the interface, it is natural that the user needs to define a higher threshold value to end up evaluating each command during a larger number of trials. When the user increases his/her ability to generate correct patterns, it is possible to decrease the threshold value, and thus the time required to obtain the resulting command.

B. Statistical Implementation with HM

As in the threshold implementation, the statistical implementation requires more than one trial to give an answer. But, instead of using the modular multi-net (MMN) system, the hierarchical model (HM) is used.

In this implementation, each trial is classified using the HM. For m different patterns, the occurrence of each one is evaluated after a pre-defined minimum number of trials (e.g. a minimum of m+1 trials). If a certain pattern reaches a certain rate of occurrence, e.g. of at least 2/m, then it is chosen and converted into a robot action. In this embodiment of the invention, 4 patterns are considered, RM, LM, UM and DM, therefore m=4. As a result, the rate of occurrence of each pattern after m+1=5 or more trials is evaluated after each trial, until one of the rates reaches at least 2/m=50%. The number of trials is limited to the heuristic value 3·(m+1)=15 in this implementation, after which the command is classified as 'unclear' and no action is taken. Both implementations are evaluated next.

EXAMPLE 4

Application to a Mobile Robot

Figure 7:
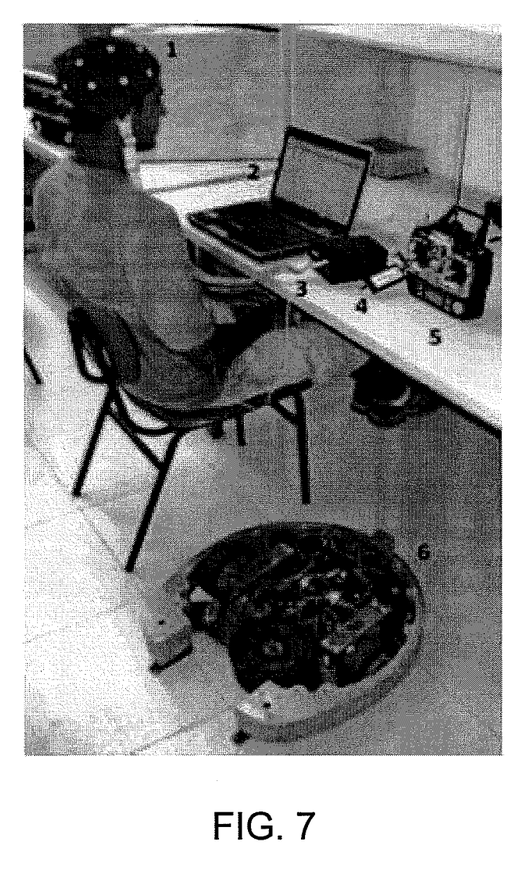
FIG. 7 shows the Experimental system: 1—Electrodes; 2—Computer; 3—EEG System in metal enclosure; 4—PCTx link; 5—RF Transmitter; 6—Mobile Robot.
Figure 8:
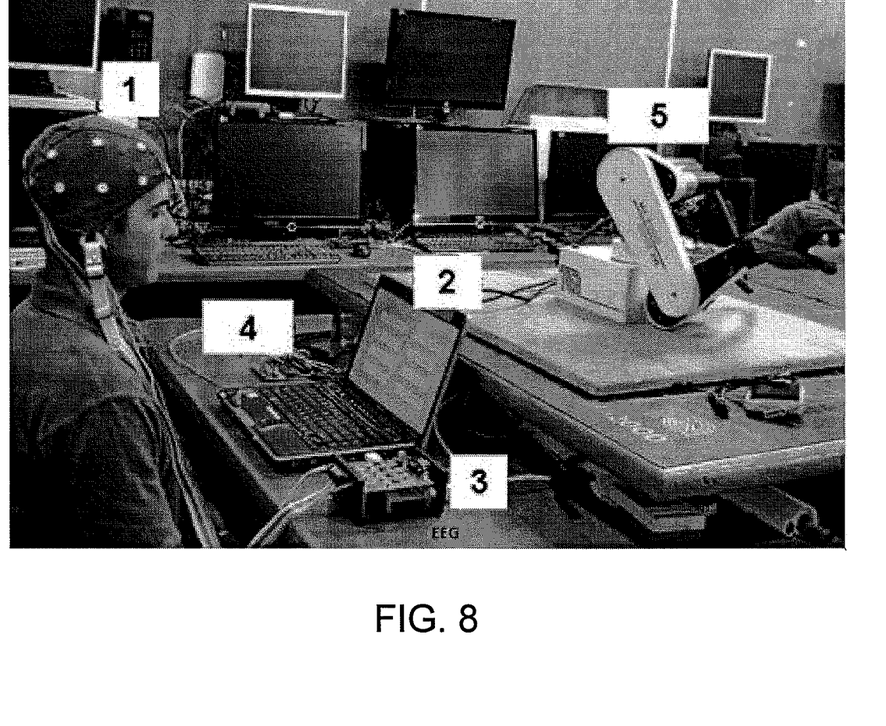
FIG. 8 is a photograph of a preferred embodiment of the device of the invention, showing the brain control of a robotic manipulator, without using an RF system: 1—Electrodes; 2—Computer; 3—EEG System in metal enclosure; 4—Electronic system to drive the manipulator; 5—Robotic Manipulator.

In one preferred embodiment, the process of the invention was used in a device (the developed BCI) for the control of a 2-wheeled 120 lb mobile robot. The chosen mobile robot, named "Touro" (seen in FIG. 7 without its top cover), was developed by the Robotics Laboratory from the Pontifical Catholic University of Rio de Janeiro (PUC-Rio). Said robot was programmed to follow radio-frequency (RF) commands and no further development was necessary. In addition, such system is analogous to an electrical wheelchair, one of the possible applications of the BCI: it is driven by only two active wheels using differential drive, and it has enough traction to carry an adult.

The BCI commands are translated to four different movements: turn 30 degrees to the right (RM), turn 30 degrees to the left (LM), move forward 500 mm (UM), and stop (DM). Note that any values other than 30 degrees and 500 mm could be used.

The communication with the robot is made through a PCTx module,[27] which receives values from an USB connection and translates it into commands to a Futaba 75 MHz RF transmitter that activates the robot.

The PC portion of the application is implemented under the MATLAB® environment, including data acquisition from the EEG A/D converter, preprocessing, processing, and sending the commands to the PCTx module. The PC used in the experiment is a 2.2 GHz Core 2 Duo notebook.

The system calibration is performed in two steps. In the first step, the user needs to carry out mental activities asked by the software, to calibrate it. First, the user is asked to trial (without any body movement) an imaginary movement of his/her feet for eleven seconds (a short beep starts the count and a long beep indicates the end of the acquisition), from which only the last ten seconds are recorded. Then, after a five second pause, the next mental activity (in this case the imaginary movement of his/her tongue) is recorded in the same way, and so on for the left and right arm activities.

Note that the five second pauses between recordings are important for the user to relax and get ready for the next step. Also, discarding the first second of each recording is important for an efficient calibration, to guarantee no auditory artifacts are present due to the short beep that signals the start of each count. This process is repeated until 700 trials are recorded (400 are used for training), taking about 20 minutes for 1-second trials and 5-second pauses.

In the second step of the calibration, the obtained dataset is used to train the classifier. The training of 4 neural networks takes less than 30 seconds in the used notebook.

After the training, the system is ready to continuously identify mental activities to control the mobile robot. Each trial takes less than 30 ms to be computed, which is insignificant if compared to the 1 s duration of each trial. Most of these 30 ms are spent on input and output interfacing, not on the methodology calculations.

Both threshold and statistical implementations are evaluated by asking the user to perform 100 times each mental activity, while looking at the mobile robot. Then, the number of successful, unclear (when no mental task is chosen within the limit number of trials) and wrong commands are stored.

Table IV shows the results for the mobile robot activation task after 400 attempts. Both implementations result in a very high rate of successful commands, near 90%, with a slightly better performance for the statistical implementation. The greatest advantage of the statistical implementation over the threshold is related with the wrong commands, only 1.25% instead of 6.75%. In the statistical implementation, most of the non-successful commands are classified as unclear, which does not translate into any action to the robot, usually a better outcome than sending a wrong command.

TABLE IV

Percentages of successful, unclear and wrong commands from the implementations using MMN and HM

|  | Successful Commands | Unclear Commands | Wrong Commands |
| --- | --- | --- | --- |
| MMN Threshold implementation | 88.75% | 4.5% | 6.75% |
| HM Statistical implementation | 91.0% | 7.75% | 1.25% |

As explained before, the number of trials to identify a command is not fixed, it depends on the user's ability to reach the threshold value (in the threshold implementation) or to obtain a high rate of a certain classification (in the statistical implementation). So, the time required to perform a robot action is not fixed. Here, the 400 attempts involved about 2,000 trials for either implementation, thus each command took an average of 2,000/400=5 trials of 1 second each, resulting in 5 seconds. Further tests are currently being conducted using trials shorter than 1 second, resulting in about 2 seconds for each command with similar hit rates as the ones shown in Table IV.

EXAMPLE 5

Conclusions

In the present invention a process and device for the synchronous operant conditioning of a BCI was developed, operating with four mental activities for the activation of a mobile robot. The BCI uses intuitive mental activities such as imaginary movement of the left arm to turn the robot left, without the need for imagining arithmetic operations or spinning solids. It was evaluated from 2,000 test trials without the mobile robot and 400 attempts with the robot. It was found that the features related to signal power in Alpha and Beta bands represent suitably the behavior of the EEG signals in the frequency-time domain during imaginary motor functions. The process of the invention not only provides a high rate of successful commands—about 90% for both threshold and statistical implementations—but also greatly decreases the number of wrong commands—as low as 1.25% for the statistical implementation—due to their concept of an 'unclear' command, when no action is taken. Each mobile robot command was identified in average after 5 trials, which could translate into 5 seconds or less depending on the chosen trial period. Further tests showed time intervals as low as 2 seconds between mobile robot commands with similar hit rates. Another advantage of both methodologies is that the system calibration for a given user takes only about 20 minutes.

Despite the relatively high number of wrong commands from the threshold implementation, the process of the invention provides means for generating combined commands, e.g. making the robot move forward-right while the user imagines the movement of both tongue and right arm. The implemented BCI can alternatively comprise an embedded Brain Machine Interface (BMI), which offers portability and improved user-friendliness.

Those skilled in the art will readily appreciate the invention, and will recognize that subtle variations in embodying the inventive concept of the invention are to be deemed with the scope of the invention and of the appended claims.

What is claimed is:

1. A process for brain controlled functions comprising the steps of:
    non-invasively obtaining brain signals acquired from near the pre-motor cortex area or the motor cortex area;
    processing said brain signals into electroencephalograph (EEG) signals; and
    transducing said EEG signals into functional commands by means of feature extraction from said EEG signals, wherein said EEG signals are classified as at least one specific mental activity having a respective pattern by:
        preprocessing said EEG signals;
        implementing classifying models for said EEG signals comprising implementing at least one or a combination of the following classifying models:
            a) an ensemble of multi-layer perceptron (MLP) artificial neural networks, said ensemble having an equal number of MLP artificial neural networks and respective patterns; and
            b) a modular multi-net (MMN) system where a certain number of neural networks are used, one for each of a respective pattern, each network classifying a feature vector as belonging or not to its respective pattern, and when more than one neural network classifies the feature vector as belonging to its respective pattern, then the classification is obtained as the one with higher output value,
        wherein the respective pattern is selected from the group consisting of right movement (RM), left movement (LM), forward movement (UM), and stop movement (DM); and
    conducting multiple trial classification to improve a hit rate of successful functional commands.

2. The process according to claim 1, wherein the step of preprocessing said EEG signals comprises: filtering noise; using a spatial filter to increase the scalp signal resolution; and extracting relevant features from the power density of the wavelet transform that are classified as specific mental activities.

3. The process according to claim 1, wherein the classifying model in b) comprises:
    i) a hierarchical model to analyze a resulting confusion matrix of the MMN system, and to verify a majority of missed classifications; and
    ii) wherein the hierarchical model comprises a hierarchical structure that divides the problem in levels, resulting in a better classification of confused patterns.

4. The process according to claim 1, wherein the step of multiple trial classification to improve the rate of successful commands comprises at least the two following implementations:
    i) an implementation providing a grade estimated to each respective pattern, said grade attributed to each output and corresponding to each respective pattern being added to a respective grade in the next trial; when a grade sum of a respective pattern reaches a predetermined limit, that respective pattern is chosen and converted; if more than one respective pattern reaches the threshold at the same trial or if no respective pattern reaches the defined threshold within the maximum number of trials, then the command is classified as 'unclear' and no action is taken; and
    ii) an implementation in which each trial is classified; for m different respective patterns, the occurrence of each one and the limit rate of occurrence are evaluated according to m; if a limit rate of occurrence the respective pattern reached, then it is chosen and converted; if the number of trials reaches an upper limit, then the command is classified as 'unclear' and no action is taken.

5. The process according to claim 1, wherein a hit rate is of about 91% or higher, or a hit rate of wrong commands about 1.25% or lower, after 400 attempts to generate a control signal.

6. A device for brain controlled functions comprising:
    a) means for non-invasively obtaining brain signals acquired from near the pre-motor cortex area or the motor cortex area;
    b) an electroencephalograph (EEG) for processing said brain signals into EEG signals; and
    c) a dedicated electronic processing board configured to transduce said EEG signals into functional commands by feature extraction from said EEG signals, wherein said EEG signals are classified as at least one specific mental activity having a respective pattern by:

i) preprocessing said EEG signals;

ii) implementing classifying models for said EEG signals comprising implementing at least one or a combination of the following classifying models:

a) an ensemble of multi-layer perceptron (MLP) artificial neural networks, said ensemble having an equal number of MLP artificial neural networks and respective patterns; and b) a modular multi-net (MMN) system where a certain number of neural networks are used, one for each of a respective pattern, each network classifying a feature vector as belonging or not to its respective pattern, and when more than one neural network classifies the feature vector as belonging to its respective pattern, then the classification is obtained as the one with higher output value;

wherein the respective pattern is selected from the group consisting of right movement (RM), left movement (LM), forward movement (UM), and stop movement (DM); and iii) implementing multiple trial classification to improve a hit rate of successful functional commands.

7. The device according to claim 6, wherein said EEG signals are preprocessed by filtering noise, increasing scalp signal resolution using a spatial filter, extracting relevant features from a power density of a wavelet transform of at least of the EEG signals.

8. The device according to claim 6, for the brain control of electromechanical devices/equipments.

9. The device according to claim 6, for the brain control of wheel chairs.

10. The device according to claim 6, for the brain control of a robotic manipulator/prosthesis.

11. The device according to claim 6, for the brain control of a computer software system with a linear function menu.

\* \* \* \* \*